(12) United States Patent
Tsukada et al.

(10) Patent No.: US 11,887,349 B2
(45) Date of Patent: Jan. 30, 2024

(54) INTEREST DETERMINATION APPARATUS, INTEREST DETERMINATION SYSTEM, INTEREST DETERMINATION METHOD, AND NON-TRANSITORY COMPUTER READABLE MEDIUM STORING PROGRAM

(71) Applicant: NEC Corporation, Tokyo (JP)

(72) Inventors: Masato Tsukada, Tokyo (JP); Hiroshi Imai, Tokyo (JP); Chisato Funayama, Tokyo (JP); Yuka Ogino, Tokyo (JP); Ryuichi Akashi, Tokyo (JP); Keiichi Chono, Tokyo (JP); Emi Inui, Tokyo (JP); Yasuhiko Yoshida, Tokyo (JP); Hiroshi Yamada, Tokyo (JP); Shoji Yachida, Tokyo (JP); Takashi Shibata, Tokyo (JP)

(73) Assignee: NEC CORPORATION, Tokyo (JP)

(*) Notice: Subject to any disclaimer, the term of this patent is extended or adjusted under 35 U.S.C. 154(b) by 195 days.

(21) Appl. No.: 17/439,898

(22) PCT Filed: Mar. 26, 2019

(86) PCT No.: PCT/JP2019/012946
§ 371 (c)(1),
(2) Date: Sep. 16, 2021

(87) PCT Pub. No.: WO2020/194529
PCT Pub. Date: Oct. 1, 2020

(65) Prior Publication Data
US 2022/0189132 A1 Jun. 16, 2022

(51) Int. Cl.
*G06V 10/25* (2022.01)
*G06V 10/60* (2022.01)
(Continued)

(52) U.S. Cl.
CPC ............. *G06V 10/25* (2022.01); *A61B 5/16* (2013.01); *G06V 10/60* (2022.01); *G06V 40/18* (2022.01)

(58) Field of Classification Search
None
See application file for complete search history.

(56) References Cited

U.S. PATENT DOCUMENTS 5,859,686 A * 1/1999 Aboutalib ............ A61B 3/113
351/221
10,416,763 B2 * 9/2019 He .................... G06V 10/141
(Continued)

FOREIGN PATENT DOCUMENTS

| CN | 108052973 A | 5/2018 |
| JP | H11-101935 A | 4/1999 |

(Continued)

OTHER PUBLICATIONS

International Search Report for PCT Application No. PCT/JP2019/012946, dated Jul. 2, 2019.
(Continued)

*Primary Examiner* — Santiago Garcia
(74) *Attorney, Agent, or Firm* — Sughrue Mion, PLLC

(57) ABSTRACT

An image acquisition unit (2) acquires an image obtained by capturing at least eyes of a target person. An object specifying unit (4) specifies an object in a line-of-sight direction of the target person using the acquired image. An incident light amount calculation unit (6) calculates an incident light amount representing an amount of light incident on the eyes of the target person using the acquired image. A reference pupil size determination unit (8) determines a reference pupil size based on the calculated incident light amount. A pupil size calculation unit (10) calculates a pupil size of the target person using the acquired image. An interest determination unit (12) determines an interest of the target person
(Continued)

in the object by comparing the determined reference pupil size with the calculated pupil size.

5 Claims, 7 Drawing Sheets

(51) Int. Cl.
*G06V 40/18* (2022.01)
*A61B 5/06* (2006.01)
*A61B 5/16* (2006.01)

(56) References Cited

U.S. PATENT DOCUMENTS

| | | | | |
|---|---|---|---|---|
| 2004/0174496 | A1* | 9/2004 | Ji | G06F 18/2431 |
| | | | | 351/209 |
| 2010/0010370 | A1 | 1/2010 | De Lemos et al. | |
| 2014/0155763 | A1* | 6/2014 | Bruce | A61B 5/01 |
| | | | | 600/484 |
| 2015/0042949 | A1* | 2/2015 | Jeglorz | G01B 9/02041 |
| | | | | 356/497 |
| 2015/0131051 | A1* | 5/2015 | Huang | A61B 3/14 |
| | | | | 351/206 |
| 2016/0248971 | A1* | 8/2016 | Tall | G06V 10/141 |
| 2017/0116740 | A1* | 4/2017 | Kimura | G06T 7/90 |
| 2017/0118403 | A1 | 4/2017 | Chu et al. | |
| 2018/0120933 | A1* | 5/2018 | Waldorf | A61B 3/112 |
| 2018/0309955 | A1* | 10/2018 | Lawrence | H04N 19/00 |
| 2018/0367769 | A1* | 12/2018 | Greenberg | G02B 27/0179 |
| 2019/0282090 | A1* | 9/2019 | Winsor | A61B 3/0025 |
| 2020/0302825 | A1* | 9/2020 | Sachs | G09B 5/02 |
| 2021/0169417 | A1* | 6/2021 | Burton | A61B 5/4857 |
| 2021/0282639 | A1* | 9/2021 | Yokoyama | G02B 27/02 |
| 2023/0011625 | A1* | 1/2023 | Babazaki | G06T 7/74 |

FOREIGN PATENT DOCUMENTS

| | | |
|---|---|---|
| JP | 2006-050233 A | 2/2006 |
| JP | 2010-197656 A | 9/2010 |
| JP | 2011-2401 A | 1/2011 |
| JP | 2017-510203 A | 4/2017 |
| WO | 2011/042989 A1 | 4/2011 |
| WO | 2015/072202 A1 | 5/2015 |
| WO | 2016/143759 A1 | 9/2016 |
| WO | 2018/100875 A1 | 6/2018 |

OTHER PUBLICATIONS

Japanese Office Action for JP Application No. 2021-508491 dated Jun. 14, 2022 with English Translation.

* cited by examiner

ABSOLUTE LUMINANCE TABLE

| AMOUNT OF INCIDENT LIGHT L | APERTURE VALUE F | SHUTTER SPEED S | TRISTIMULUS VALUE Y |
|---|---|---|---|
| L1 | F1 | S1 | Y1 |
| L1 | F1 | S2 | Y2 |
| L1 | F2 | S1 | Y3 |
| L1 | F2 | S2 | Y4 |
| L2 | F1 | S1 | Y5 |
| L2 | F1 | S2 | Y6 |
| L2 | F2 | S1 | Y7 |
| L2 | F2 | S2 | Y8 |

Fig. 5

REFERENCE PUPIL SIZE TABLE

| INCIDENT LIGHT AMOUNT EE(lx) | REFERENCE PUPIL SIZE D0(mm) |
|---|---|
| 0.01 | 7.0 |
| 1.0 | 6.0 |
| 100 | 3.0 |
| 10000 | 2.1 |

Fig. 7

INTEREST DETERMINATION APPARATUS, INTEREST DETERMINATION SYSTEM, INTEREST DETERMINATION METHOD, AND NON-TRANSITORY COMPUTER READABLE MEDIUM STORING PROGRAM

This application is a National Stage Entry of PCT/JP2019/012946 filed on Mar. 26, 2019, the contents of all of which are incorporated herein by reference, in their entirety.

TECHNICAL FIELD

The present disclosure relates to an interest determination apparatus, an interest determination system, an interest determination method, and a non-transitory computer readable medium storing a program.

BACKGROUND ART

For example, a method of determining an interest of a customer or the like at a store in a product has been studied. Here, it is known that human emotion and pupil diameter are related, and a method for understanding an interest of a person from a size of the pupil can be considered. On the other hand, since the pupil diameter largely responds to the brightness (illuminance and luminance) of a visual recognition object, unless the pupil diameter reaction to the brightness of the visual recognition object is removed, there is a possibility that the pupil diameter reaction in accordance with the accurate degree of attention may not be obtained. In connection with this technique, Patent Literature 1 discloses a viewer emotion determination apparatus for diagnosing an emotion (feeling) of a viewer looking at a visual scene including a specific object toward the specific object.

In the apparatus according to Patent Literature 1, when the visual recognition object is a video display, the luminance of the video display is changed, the pupil diameter of the viewer responding to the change in the luminance is obtained and accumulated as relationship data between a basic luminance and the pupil diameter. The apparatus according to Patent Literature 1 measures the pupil diameter of the viewer when the viewer visually recognizes a target object, and at the same time, measures luminance for a viewing range by a luminance meter. The apparatus according to Patent Literature 1 obtains the pupil diameter corresponding only to a degree of attention to the object by subtracting a value of the pupil diameter corresponding to the luminance at the time of visually recognizing the object in the accumulated relationship data between the basic luminance and the pupil diameter from the value of the pupil diameter at the time of visually recognizing the object.

Further, in the apparatus according to Patent Literature 1, when the visual recognition object is a visual scene other than the video display, an eyeball capturing apparatus, a face capturing apparatus, a visual scene capturing apparatus, and a brightness measuring apparatus are integrally mounted on the viewer's head and the measurement is performed. In such a case, the apparatus according to Patent Literature 1 applies illuminance indicating the brightness of the viewing range instead of the luminance, and performs measurement using an illuminance meter instead of a luminance meter. In this case, the "relationship data between the basic illuminance and the pupil diameter" corresponding to the "relationship data between the basic luminance and the pupil diameter" can be obtained by preparing a room which can change the basic luminance and then measuring the pupil diameter in the room.

CITATION LIST

Patent Literature

Patent Literature 1: International Patent Publication No. WO2011/042989

SUMMARY OF DISCLOSURE

Technical Problem

In the technique described in Patent Literature 1, the luminance and illuminance cannot be measured unless the viewer wears special apparatuses such as the luminance meter, the eyeball capturing apparatus, the face capturing apparatus, the visual scene capturing apparatus, and the brightness measuring apparatus. Therefore, according to the technique disclosed in Patent Literature 1, it is difficult to determine an interest of the viewer (a target person) in the object under any environment such that the viewer need not wear the special apparatuses.

An object of the present disclosure is to provide an interest determination apparatus, an interest determination system, an interest determination method, and a program capable of determining an interest of a target person in an object under any environment.

Solution to Problem

An interest determination apparatus according to the present disclosure includes: image acquisition means for acquiring an image obtained by capturing at least eyes of a target person; object specifying means for specifying an object in a line-of-sight direction of the target person using the image; incident light amount calculation means for calculating an incident light amount representing an amount of light incident on the eyes of the target person using the image; reference pupil size determination means for determining a reference pupil size based on the incident light amount; pupil size calculation means for calculating a pupil size of the target person using the image; and interest determination means for determining an interest of the target person in the object by comparing the reference pupil size with the pupil size.

An interest determination system according to the present disclosure includes: at least one imaging apparatus; and an interest determination apparatus. The interest determination apparatus includes image acquisition means for acquiring an image captured by the imaging apparatus and obtained by capturing at least eyes of a target person; object specifying means for specifying an object in a line-of-sight direction of the target person using the image; incident light amount calculation means for calculating an incident light amount representing an amount of light incident on the eyes of the target person using the image; reference pupil size determination means for determining a reference pupil size based on the incident light amount; pupil size calculation means for calculating a pupil size of the target person using the image; and interest determination means for determining an interest of the target person in the object by comparing the reference pupil size with the pupil size.

An interest determination method according to the present disclosure includes: acquiring an image obtained by capturing at least eyes of a target person; specifying an object in a line-of-sight direction of the target person using the image; calculating an incident light amount representing an amount of light incident on the eyes of the target person using the image; determining a reference pupil size based on the incident light amount; calculating a pupil size of the target person using the image; and determining an interest of the target person in the object by comparing the reference pupil size with the pupil size.

A program according to the present disclosure causes a computer to execute: acquiring an image obtained by capturing at least eyes of a target person; specifying an object in a line-of-sight direction of the target person using the image; calculating an incident light amount representing an amount of light incident on the eyes of the target person using the image; determining a reference pupil size based on the incident light amount; calculating a pupil size of the target person using the image; and determining an interest of the target person in the object by comparing the reference pupil size with the pupil size.

Advantageous Effects of Disclosure

According to the present disclosure, it is possible to provide an interest determination apparatus, an interest determination system, an interest determination method, and a program capable of determining an interest of a target person in an object under any environment.

BRIEF DESCRIPTION OF DRAWINGS

FIG. 5 shows an example of an absolute luminance table used by an object luminance calculation unit according to the first example embodiment;

FIG. 7 shows an example of a reference pupil size table according to the first example embodiment.

DESCRIPTION OF EXAMPLE EMBODIMENTS (Overview of Example Embodiment According to the Present Disclosure)

Figure 1:
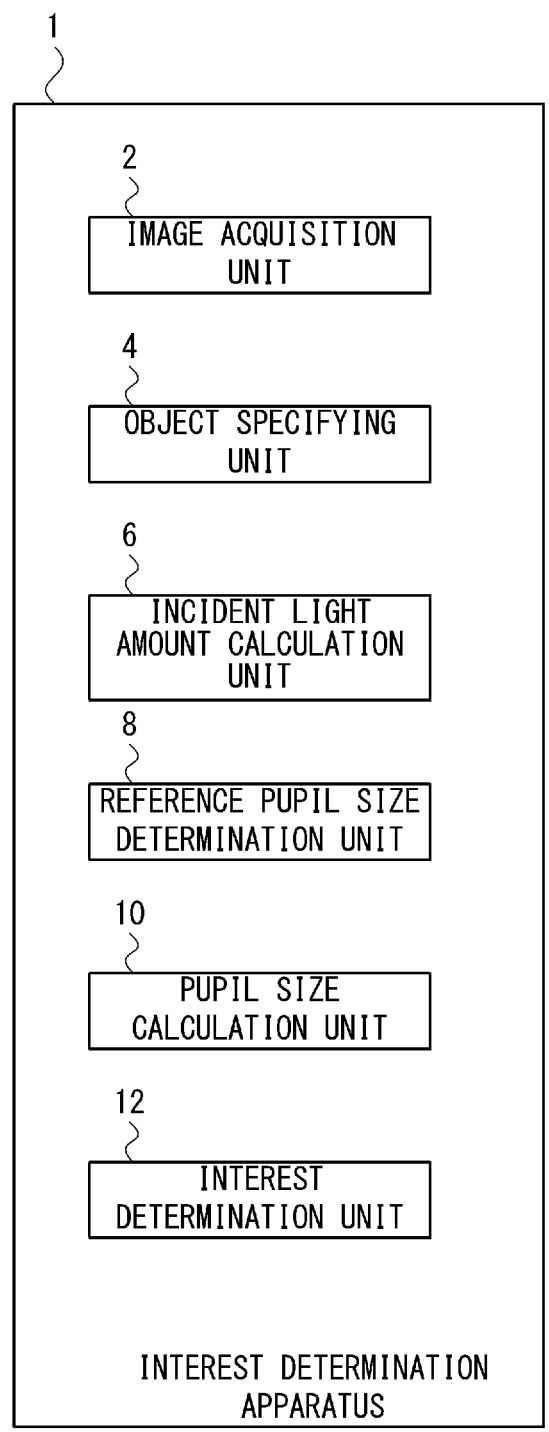
FIG. 1 shows an overview of an interest determination apparatus according to an example embodiment of the present disclosure.

Prior to the description of an example embodiment of the present disclosure, an overview of the example embodiment of the present disclosure will be described. FIG. 1 is a diagram showing an overview of an interest determination apparatus 1 according to the example embodiment of the present disclosure. The interest determination apparatus 1 is, for example, a computer.

The interest determination apparatus 1 includes an image acquisition unit 2, an object specifying unit 4, an incident light amount calculation unit 6, a reference pupil size determination unit 8, a pupil size calculation unit 10, and an interest determination unit 12. The image acquisition unit 2 functions as image acquisition means. The object specifying unit 4 functions as object specifying means. The incident light amount calculation unit 6 functions as incident light amount calculation means. The reference pupil size determination unit 8 functions as reference pupil size determination means. The pupil size calculation unit 10 functions as pupil size calculation means. The interest determination unit 12 functions as interest determination means.

The image acquisition unit 2 acquires an image in which at least target person's eyes are captured. The target person is a person to be subjected to interest determination. The object specifying unit 4 specifies an object in a line-of-sight direction of the target person using the acquired image. Here, the object is an object which the target person is paying attention to, and is an object for determining whether the target person is interested or not. The incident light amount calculation unit 6 calculates an incident light amount representing an amount of light incident on the target person's eyes using the acquired image. The reference pupil size determination unit 8 determines a reference pupil size based on the calculated incident light amount. The pupil size calculation unit 10 calculates the pupil size of the target person using the acquired image. The interest determination unit 12 determines the interest of the target person in the object by comparing the determined reference pupil size with the calculated pupil size.

The interest determination apparatus 1 according to this example embodiment uses the acquired image to specify the object in the line-of-sight direction of the target person, and calculates the incident light amount on the target person's eyes. In this way, it is possible to determine the interest of the target person in the target object without the target person wearing the special apparatuses such as the luminance meter, the eyeball capturing apparatus, the face capturing apparatus, the visual scene capturing apparatus, and the brightness measuring apparatus. Therefore, the interest determination apparatus 1 according to this example embodiment can determine the interest of the target person in the object under any environment.

Note that the interest of the target person in the object can be determined under any environment also by using the interest determination method executed by the interest determination apparatus 1. In addition, the interest of the target person in the object can be determined under any environment also by using a program for executing the interest determination method. Furthermore, the interest of the target person in the object can be determined under any environment also by using the interest determination apparatus 1 and at least one imaging apparatus (camera).

First Example Embodiment

An example embodiment will be described below with reference to the drawings. For clarity of description, the following descriptions and drawings have been omitted and simplified as appropriate. In each of the drawings, the same elements are denoted by the same reference signs, and repeated descriptions are omitted as necessary.

Figure 2:
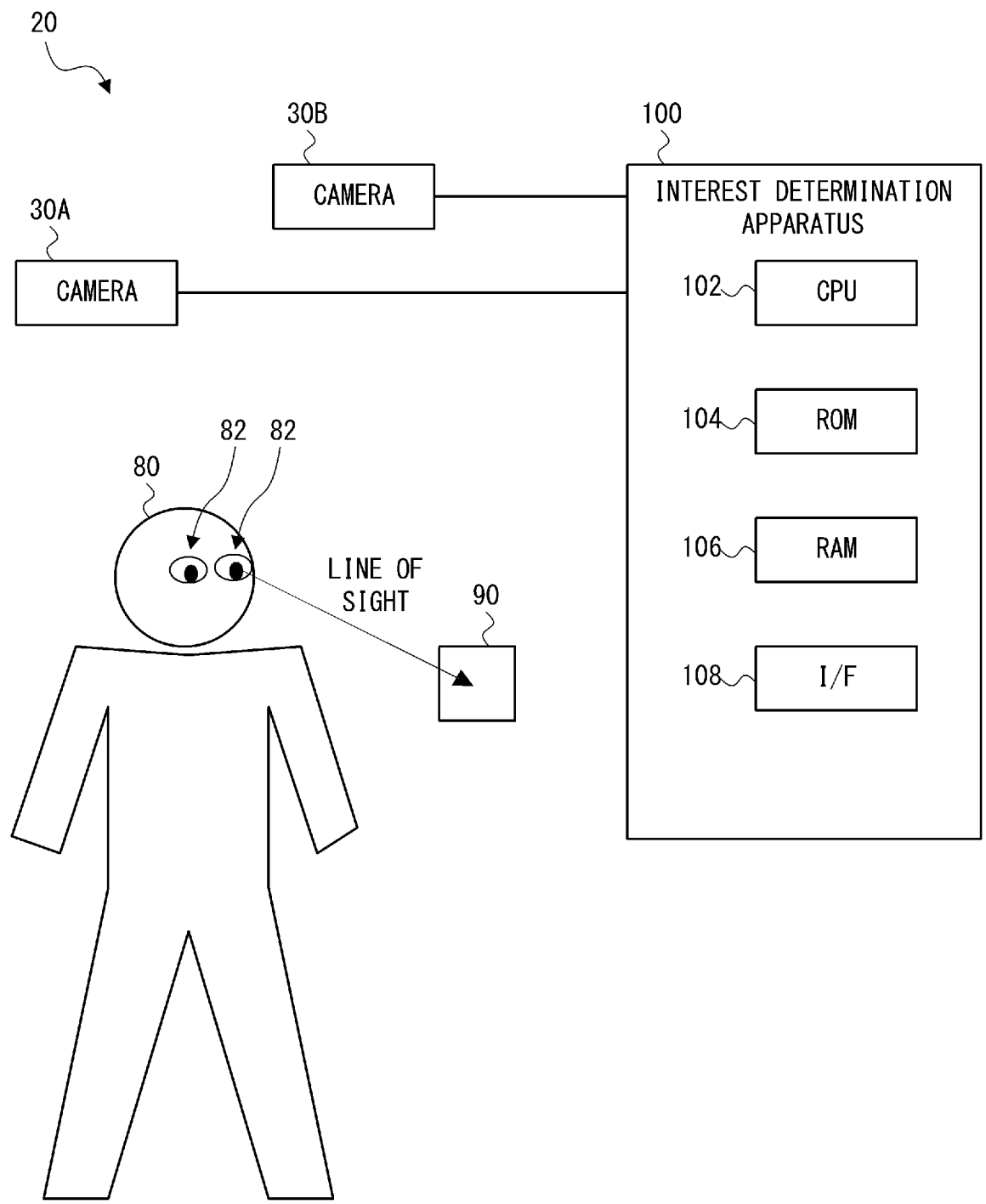
FIG. 2 shows a configuration of an interest determination system according to the first example embodiment.

FIG. 2 shows a configuration of an interest determination system 20 according to the first example embodiment. The interest determination system 20 according to the first example embodiment includes cameras 30A and 30B and an interest determination apparatus 100. The interest determination apparatus 100 corresponds to the interest determination apparatus 1 shown in FIG. 1. Hereinafter, when the cameras 30A and 30B are described without distinction between them, they may be referred to as cameras 30. The cameras 30 are, for example, capturing (imaging) apparatuses installed in a store or the like.

The interest determination system 20 may include three or more cameras 30. Alternatively, the interest determination system 20 may include only one camera 30. That is, the interest determination system 20 includes at least one imaging apparatus (the camera 30).

The cameras 30 capture eyes 82 of a target person 80. The cameras 30 generate images (image data) in which at least the target person's eyes are captured. The cameras 30 can capture an object 90 in a line-of-sight direction of the eyes 82 of the target person 80. That is, the object 90 is an object at which the target person 80 gazes. The camera 30A may capture the target person 80 (the eyes 82), and the camera 30B may capture the object 90. That is, the camera 30A may be provided at a position where the target person 80 can be captured. The camera 30B may be provided at a position where the object 90 can be captured. However, one camera 30 (e.g., the camera 30B) may capture the eyes 82 of the target person 80 and the object 90. Hereinafter, the term "image" may also mean "image data indicating an image" to be processed in information processing. The image may be a still image or a moving image.

The interest determination apparatus 100 is, for example, a computer. The interest determination apparatus 100 is connected to the cameras 30 through a wire or wirelessly so that communication is possible between them. The interest determination apparatus 100 acquires an image in which at least the eyes 82 of the target person 80 are captured. The interest determination apparatus 100 specifies an object in the line-of-sight direction of the target person 80 using the image. The interest determination apparatus 100 calculates the incident light amount representing an amount of light incident on the eyes 82 of the target person 80 using the image. The interest determination apparatus 100 determines the reference pupil size based on the calculated incident light amount. The interest determination apparatus 100 calculates the pupil size of the target person using the image. Then, the interest determination apparatus 100 determines the interest of the target person 80 in the object 90 by comparing the determined reference pupil size with the calculated pupil size.

The interest determination apparatus 100 includes, as major hardware configurations, a CPU 102 (Central Processing Unit), a ROM 104 (Read Only Memory), a RAM 106 (Random Access Memory), and an Interface (IF) unit 108. The CPU 102, the ROM 104, the RAM 106, and the interface unit 108 are connected to each other via a data bus or the like.

The CPU 102 functions as an arithmetic device for performing control processing, arithmetic processing, and the like. The ROM 104 includes a function for storing a control program, an arithmetic program, and so on to be executed by the CPU 102. The RAM 106 includes a function for temporarily storing processing data and so on. The interface unit 108 inputs and outputs signals to and from the outside through the wire or wirelessly. The interface unit 108 receives an operation of data input by a user and displays information to the user. For example, the interface unit 108 communicates with the cameras 30.

Figure 3:
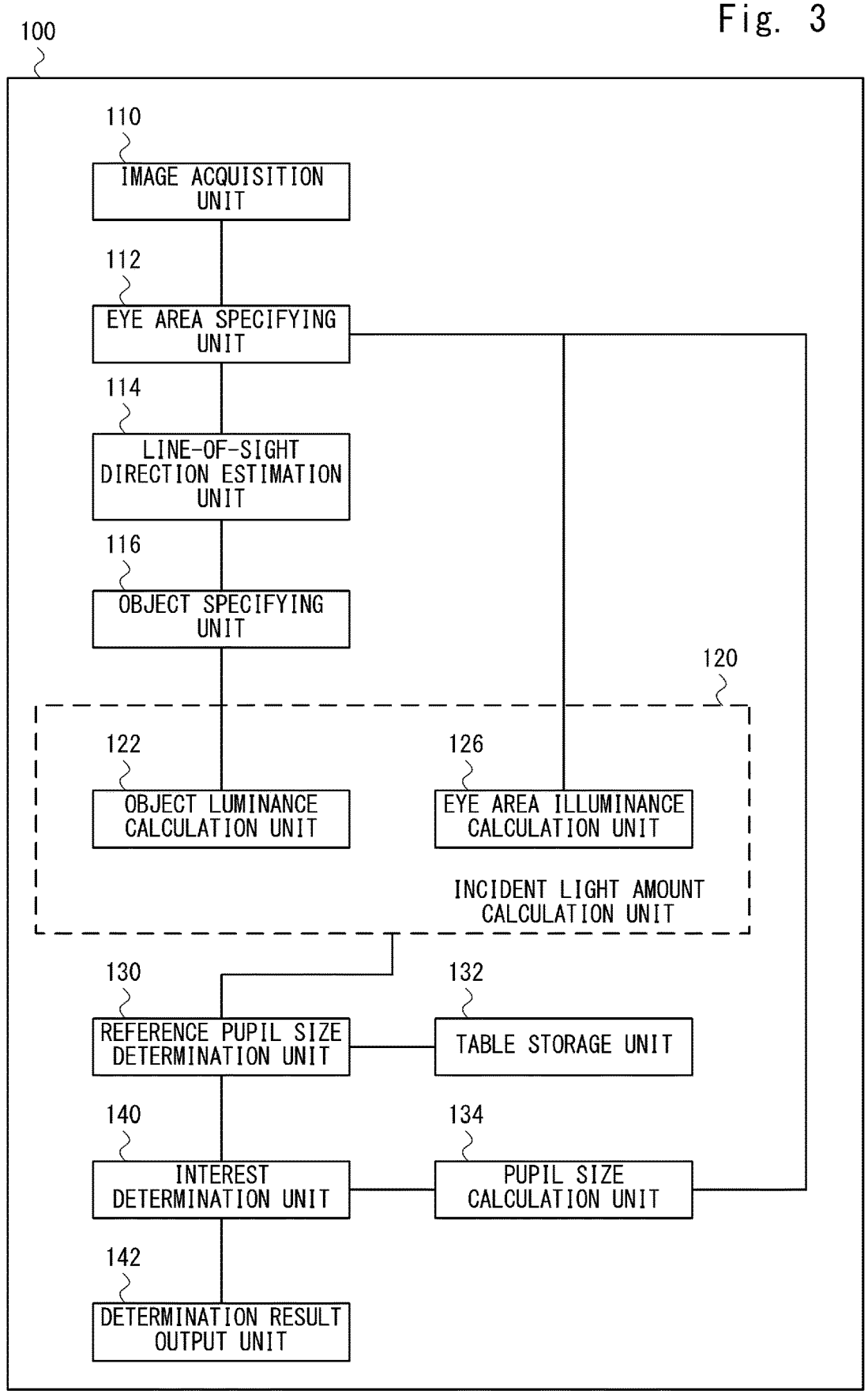
FIG. 3 is a functional block diagram showing the interest determination apparatus according to the first example embodiment.

FIG. 3 is a functional block diagram showing the interest determination apparatus 100 according to the first example embodiment. The interest determination apparatus 100 includes an image acquisition unit 110, an eye area specifying unit 112, a line-of-sight direction estimation unit 114, an object specifying unit 116, and an incident light amount calculation unit 120. The interest determination apparatus 100 also includes a reference pupil size determination unit 130, a table storage unit 132, a pupil size calculation unit 134, an interest determination unit 140, and a determination result output unit 142. The incident light amount calculation unit 120 includes an object luminance calculation unit 122 and an eye area illuminance calculation unit 126.

The image acquisition unit 110, the eye area specifying unit 112, the line-of-sight direction estimation unit 114, the object specifying unit 116, and the incident light amount calculation unit 120 function as the image acquisition means, eye area specifying means, line-of-sight direction estimation means, the object specifying means, and the incident light amount calculation means, respectively. The object luminance calculation unit 122 and the eye area illuminance calculation unit 126 function as object luminance calculation means and eye area illuminance calculation means, respectively. The reference pupil size determination unit 130, the table storage unit 132, the pupil size calculation unit 134, and the determination result output unit 142 function as reference pupil size determination means, table storage means, pupil size calculation means, and determination result output means, respectively.

The components shown in FIG. 3 can be implemented, for example, by the CPU 102 executing the program stored in the ROM 104. In addition, necessary programs may be recorded on a non-volatile recording medium and installed as required. Each of the components is not limited to being implemented by software as described above, and instead may be implemented by hardware such as some kind of a circuit element. Further, one or more of the components may be implemented by physically separate pieces of hardware, respectively. The specific functions of the components will be described later.

Figure 4:
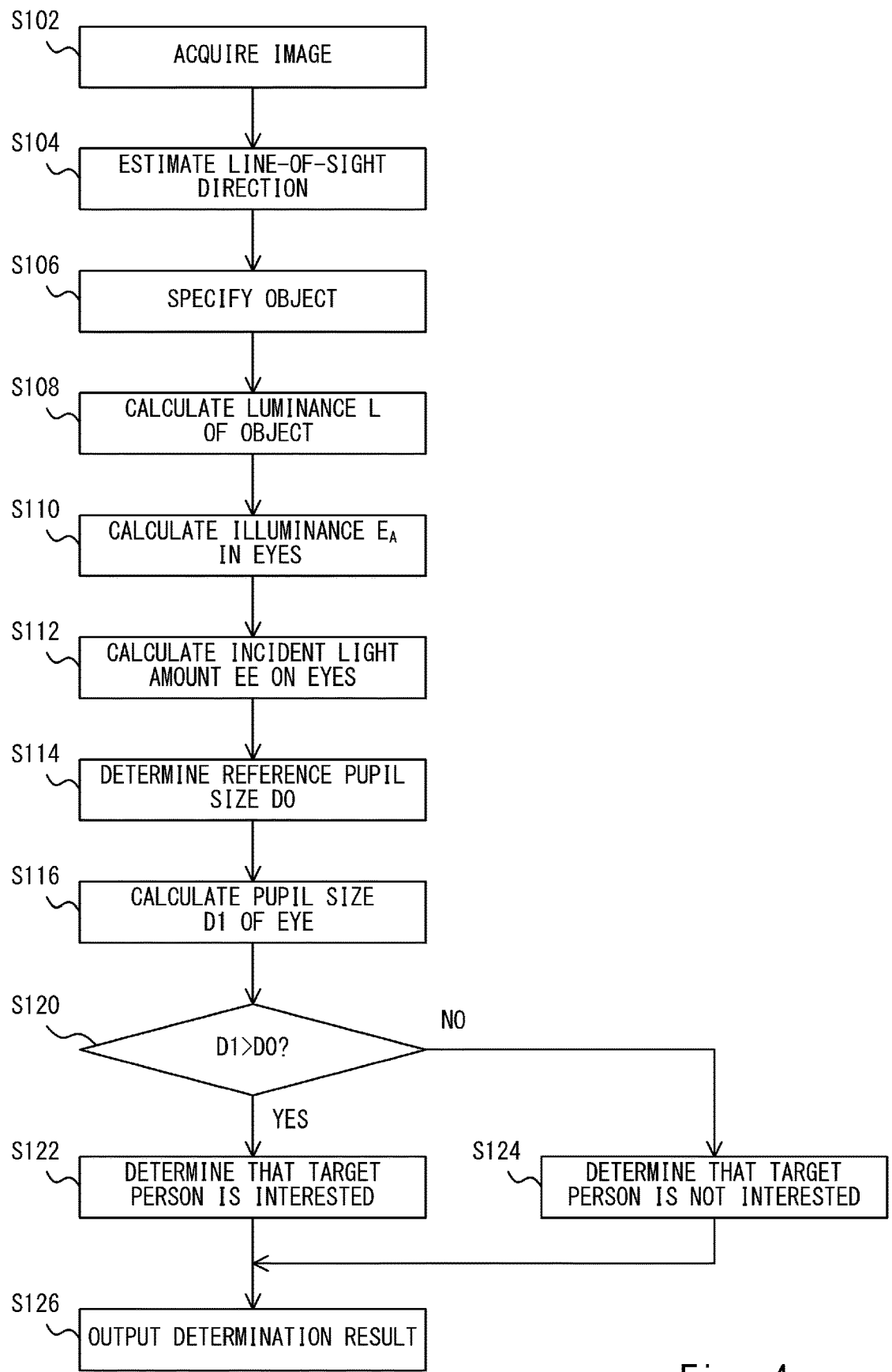
FIG. 4 is a flowchart showing an interest determination method performed by the interest determination apparatus according to the first example embodiment.

FIG. 4 is a flowchart showing an interest determination method performed by the interest determination apparatus 100 according to the first example embodiment. The image acquisition unit 110 acquires the image from the cameras 30 via the interface unit 108 (Step S102). Specifically, the image acquisition unit 110 may acquire, from the camera 30A, the image in which the eyes 82 of the target person 80 are captured. The image acquisition unit 110 may also acquire, from the camera 30B, the image in which the object 90 is captured.

Next, the interest determination apparatus 100 estimates the line-of-sight direction of the target person 80 using the image acquired in the process of Step S102 (Step S104). Specifically, the eye area specifying unit 112 detects an eye area of the eyes 82 of the target person 80 from the image output from the camera 30A. The detection of the eye area can be implemented by, for example, an object detection technique using a learning model obtained by machine learning. Further, the eye area specifying unit 112 detects a white eye area (sclera) in the detected eye area. Then, the eye area specifying unit 112 acquires color information (R, G, B) of the white eye area.

The line-of-sight direction estimation unit 114 estimates the line-of-sight direction of the target person 80 from the detected eye area. The estimation of the line-of-sight direction can be implemented by existing methods. For example, the line-of-sight direction estimation unit 114 detects an orientation of the face of the target person 80 using the image obtained by capturing the face of the target person 80. The line-of-sight direction estimation unit 114 detects a position of a pupil center in the eye area. The line-of-sight direction estimation unit 114 estimates the line-of-sight direction from the orientation of the face and the position of the pupil center.

Next, the object specifying unit 116 specifies the object 90 in the line-of-sight direction of the target person 80 (Step S106). Specifically, the object specifying unit 116 specifies the object 90 using the image output from the camera 30B.

More specifically, the object specifying unit 116 geometrically converts the line-of-sight direction estimated in the process of S104, from the position and angle of view of each of the cameras 30A and 30B, from the coordinate system of the image output from the camera 30A into the coordinate system of the image output from the camera 30B. In this manner, the object specifying unit 116 maps a line-of-sight direction vector to the image output from the camera 30B. The object specifying unit 116 specifies an object located ahead of the line-of-sight direction vector as the object 90.

Next, the incident light amount calculation unit 120 calculates the incident light amount representing the amount of light incident on the eyes 82 of the target person 80 using the image acquired in the process of S102 (S108 to S112). The object luminance calculation unit 122 calculates luminance L of the object 90 using the image acquired in the process of Step S102 (Step S108). That is, the object luminance calculation unit 122 (the incident light amount calculation unit 120) calculates the luminance L in the area of the object 90 in the image acquired in the process of Step S102. An example of a specific method of calculating the luminance L will be described later.

The eye area illuminance calculation unit 126 calculates illuminance $E_A$ in the eyes 82 of the target person 80 using the image acquired in the process of S102 (Step S110). That is, the eye area illuminance calculation unit 126 (the incident light amount calculation unit 120) calculates the illuminance $E_A$ in the eyes 82 of the target person 80 from the luminance (color information) in the areas (the white eye areas) of the eyes 82 of the target person 80 in the image acquired in the process of S102. An example of a specific method of calculating the illuminance $E_A$ will be described later.

The incident light amount calculation unit 120 calculates an incident light amount EE on the eyes 82 of the target person 80 from the luminance L calculated in the process of Step S108 and the illuminance $E_A$ calculated in the process of Step S110 (Step S112). Specifically, the incident light amount calculation unit 120 calculates the incident light amount EE using a function EE=f (L, $E_A$) indicating the relationship between the incident light amount EE, the luminance L, and the illuminance $E_A$. An example of a specific method of calculating the incident light amount EE will be described later.

Specific examples of the processes of S108 to S112 will be described below.

First, a method of calculating the luminance L of the object 90 using the image (Step S108) will be described. The object luminance calculation unit 122 calculates the luminance L of the object 90 in a color image captured by the camera 30B. The color image shall be represented in an RGB color space. It is assumed that the chromaticity of the RGB phosphor and the chromaticity of white for the RGB color space can be specified in advance as color characteristics of the camera 30B. It is also assumed that RGB data (color information) can be uniquely converted into a tristimulus values XYZ.

An example of the conversion method will be described below. The relationship between the RGB values of the input image and the tristimulus values XYZ is determined as in the following Formula 1.

[Formula 1]

$$\begin{pmatrix} X \\ Y \\ Z \end{pmatrix} = M_{RX} \begin{pmatrix} R \\ G \\ B \end{pmatrix} \quad (1)$$

Here, in Formula 1, $M_{RX}$ is a 3×3 transformation matrix. The captured image output from the camera is commonly represented in the RGB space, which has been subjected to gamma correction, and the RGB space in Formula 1 has linear characteristics ($\gamma$=1.0), which has not been subjected to gamma correction. Note that the conversion formula is not limited to the above Formula 1, and may be other formulas as long as the RGB values can be uniquely converted into the XYZ values.

For example, the conversion formula may be defined as in the following Formula 2 with an addition of a quadratic term.

[Formula 2]

$$\begin{pmatrix} X \\ Y \\ Z \end{pmatrix} = M'_{RX} \begin{pmatrix} R \\ G \\ B \\ R^2 \\ G^2 \\ B^2 \\ R \cdot G \\ G \cdot B \\ B \cdot R \end{pmatrix} \quad (2)$$

In Formula 2, $M'_{RX}$ is a 3×9 transformation matrix. Note that $M_{RX}$ and $M'_{RX}$ can be calculated in advance by performing color calibration of a camera using a known color patch.

By obtaining information about an aperture value F of a camera lens, a shutter speed and a gain at the time of capturing, the tristimulus value Y representing the brightness can be converted into absolute luminance L (cd/m²). That is, the object luminance calculation unit 122 (the incident light amount calculation unit 120) may calculate the absolute luminance L in the area of the object 90 in the image.

Here, an example of the method for converting the tristimulus value Y calculated by Formula 1 or Formula 2 into the absolute luminance Y (cd/m²) will be described. Commonly, in capturing by a camera, an aperture value F of a lens, a shutter speed and a gain are set in order to obtain proper exposure. Here, it is assumed that the gain is set to 1.0. In this case, the tristimulus value Y corresponding to the pixel value (R, G, B) of the captured image with respect to the absolute luminance L which is the amount of light incident on the camera can be determined by two variables of the lens aperture value F and the shutter speed.

First, the camera to be used is calibrated in advance. Specifically, from the pixel values (R, G, B) of the captured image when the amount of incident light (the absolute luminance L (cd/m²)), the lens aperture value F, and a shutter speed S are varied, the relationship between the tristimulus value Y obtained by Formula 1 or Formula 2 and these values is obtained. By this calibration, an absolute luminance table (LUT: Lookup table) for obtaining the absolute luminance L, which is the amount of incident light corresponding to the lens aperture value F, the shutter speed S, and the tristimulus value Y, is generated (see FIG. 5).

The lens aperture value F and the shutter speed S of the camera at the time of capturing are recorded, and the tristimulus value Y corresponding to the pixel value (R, G, B) of the area of the object 90 in the image captured under such conditions is calculated. By using the LUT, the absolute luminance L (cd/m$^2$), which is the amount of incident light for the tristimulus value Y, etc., is determined. When the LUT is referred to, an average value of the tristimulus value Y corresponding to each pixel may be used. Alternatively, the absolute luminance may be calculated for each tristimulus value corresponding to each pixel using the LUT, and the average value of the absolute luminance obtained for each pixel may be calculated as the absolute luminance L.

FIG. 5 is a diagram showing an example of the absolute luminance table (LUT) used by the object luminance calculation unit 122 according to the first example embodiment. The absolute luminance table may be stored in the table storage unit 132 described later, and when this absolute luminance table (LUT) is created, an image of a perfect (reference) white plate is captured while the aperture value F and the shutter speed S are changed. In the example of FIG. 5, the amounts of light incident on the camera 30 from the perfect white plate are L1 and L2, the aperture values are F1 and F2, and the shutter speeds are S1 and S2. Then, the tristimulus values Y corresponding to the pixel value of each captured image when captured under eight combinations of the above conditions are obtained by Formula 1 or Formula 2, so that the LUT as shown in FIG. 5 is generated.

For example, the object luminance calculation unit 122 calculates a tristimulus value Yx from the pixel value of the image captured at the aperture value F1 and the shutter speed S2. Then, the object luminance calculation unit 122 compares the tristimulus values Y2 and Y6 at the aperture value F1 and the shutter speed S2 of the LUT shown in FIG. 5 with the tristimulus value Yx, and calculates an amount Lx of incident light by interpolation or the like which is an existing method. Note that, when the LUT is created, images may be captured under many conditions instead of the eight combinations of conditions described above, so that the information amount of the LUT may be expanded. By doing so, a more accurate amount of incident light can be obtained.

Note that the relationship among the amount of incident light, the lens aperture value F, the shutter speed S, and the image output value (pixel value) may differ depending on the model of the camera, the individual difference, etc. Therefore, by performing the calibration for each camera, it is possible to calculate the absolute luminance L (cd/m$^2$) with higher accuracy.

Next, the method of calculating the illuminance $E_A$ (S110), by environmental light, in the eyes 82 of the target person 80 using the image will be described. The eye area illuminance calculation unit 126 calculates apparent irradiance at each pixel position of a reflector in the image. In this example, the reflector corresponds to the white eye area (sclera) of the eyes 82. Therefore, the eye area illuminance calculation unit 126 calculates the illuminance in the eyes 82 of the target person 80 from the color information of the white eye area.

Figure 6:
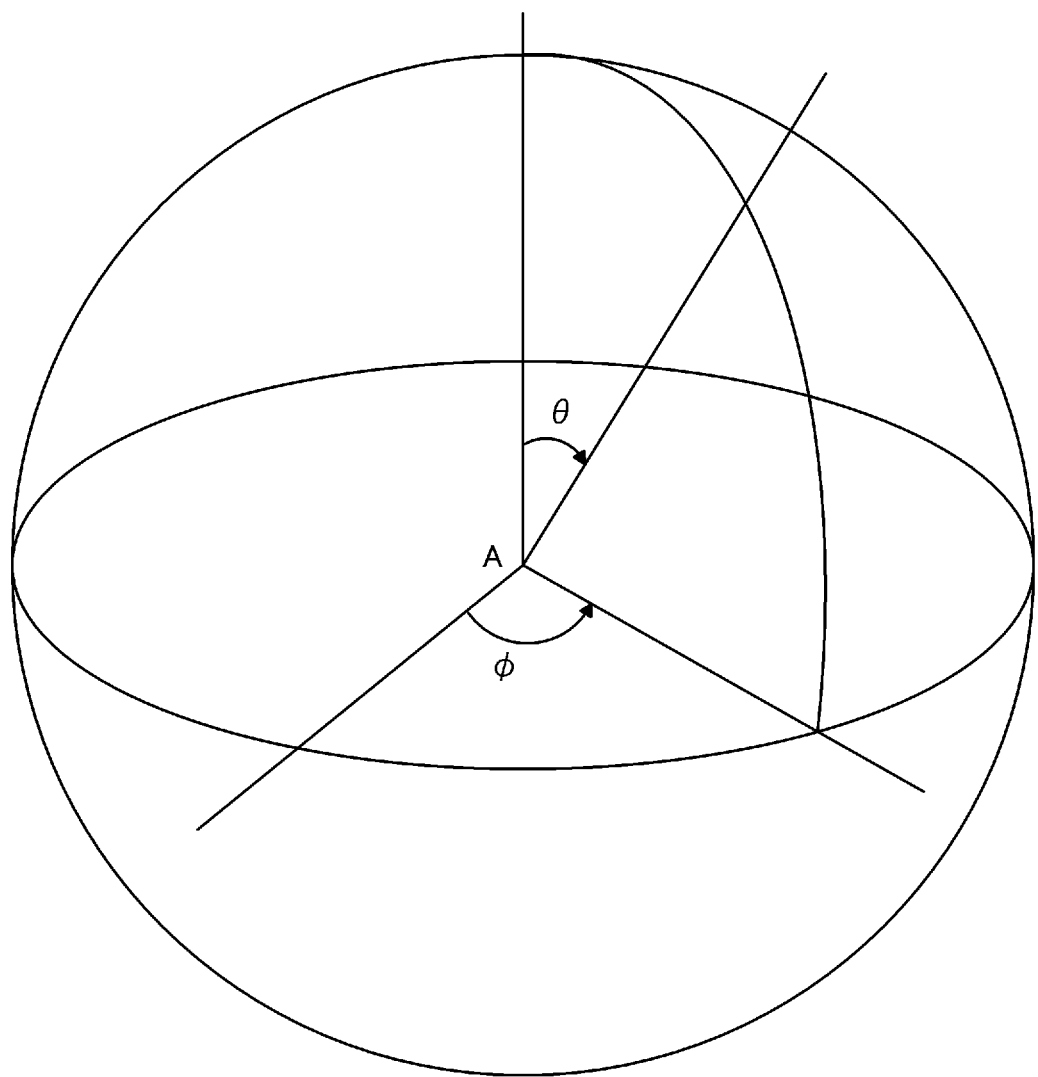
FIG. 6 is a diagram for explaining a method of calculating irradiance according to the first example embodiment.

FIG. 6 is a diagram for explaining the method of calculating the irradiance according to the first example embodiment. FIG. 6 shows an all-around light environment model considering a surface light source. In this model, assuming that a point of the reflector (the white eye area) is located at a center A of the sphere, and there is no shielding object blocking between the light source and the center A, a radiance luminance distribution of the light source from the entire surrounding is observed. This radiance luminance distribution is defined as L (θ, φ). Here, θ represents a zenith angle, and φ represents an azimuth angle.

The illuminance $E_A$ at the center A is an integral of incident light energy received from the light source represented by a minute solid angle $d\omega_i$ represented by a minute zenith angle $d\theta_i$ and a minute azimuth angle $d\omega_i$ in all directions, as shown in the following Formula 3.

[Formula 3]

$$E_A = \int_{-\pi}^{\pi} \int_{0}^{\frac{\pi}{2}} L_i(\theta_i, \varphi_i) \cos\theta_i \sin\theta_i d\theta_i d\varphi_i \qquad (3)$$

The above calculation is performed on the condition that reflection characteristic of the light of the reflector is a Lambertian reflection. Here, in the case of the sclera (white eye), although not necessarily considered as a Lambertian reflection, the light reflected at the center A is in the form of integration of the ambient environmental light incident on the center A from all directions, and is constant regardless of the viewpoint direction, because the situation is such that the minute object, which is the eye, is observed from a distance away from the object. Therefore, it can be said that the above calculation method is appropriate.

Next, if a surface reflectance $S_A$ (i.e., color) of the reflector (the white eye area) at the center A is known, a luminance value $I_A$ of the reflector recorded as an image is expressed by a product of the illuminance $E_A$ and the surface reflectance $S_A$ of the reflector, as shown in Formula 4 below. Here, the luminance value $I_A$ may be an absolute luminance value which can be determined from the tristimulus value Y calculated using Formula 1 or Formula 2 above and the aperture value F, the shutter speed, and the gain of the camera lens at the time of capturing.

[Formula 4]

$$I_A = \int_{-\pi}^{\pi} \int_{0}^{\frac{\pi}{2}} S_A L_i(\theta_i, \varphi_i) \cos\theta_i \sin\theta_i d\theta_i d\varphi_i = S_A E_A \qquad (4)$$

The luminance value $I_A$ reflects a spectral sensitivity characteristic of the camera expressed as a function of a wavelength λ of light. If the spectral sensitivity characteristic of the camera is approximated by a delta function, the wavelength λ can be regarded as a constant. Therefore, the luminance value $I_A^k$ (k is r, g, b) at the point A is expressed by the following Formula 5.

[Formula 5]

$$I_A^k = \tau^k S_A^k E_A^k \qquad (5)$$

Here, $\tau^k$ is a camera gain. That is, from Formula 5, illuminance $E_A^k$ at the point A (the white eye area) can be calculated from the luminance value $I_A$ (the color information) at the point A and the camera gain. Here, the illuminance $E_A$ of visible light at the point A (the white eye area) can be obtained by adding $E_A^r$, $E_A^g$, and $E_A^b$. Therefore, the illuminance $E_A$ is calculated from the color information of the white eye area.

Next, a method of calculating the incident light amount EE (S112) will be described. By the above calculation, the absolute luminance L of the light from the object 90 seen by the target person 80 and the illuminance $E_A$ in the eyes 82 (the eye area) of the target person 80 are obtained. Here, illuminance E1 (lx) in the eye area illuminated by the light with the luminance L (cd/m²) from the object 90 seen by the target person 80 can be expressed by the following Formula 6.

$$E1 = L \cdot \pi \qquad (6)$$

The illuminance EE (the incident light amount) in consideration of the influence of the light from the object 90 of interest to the target person 80 under a certain illumination can be expressed by the following Formula 7.

$$EE = E1 + E_A \qquad (7)$$

Therefore, the incident light amount calculation unit 120 calculates the incident light amount EE from the luminance L calculated in the process of S108 and the illuminance $E_A$ calculated in the process of S110 using Formulas 6 and 7.

Next, the reference pupil size determination unit 130 determines a reference pupil size D0 using the incident light amount EE calculated in the process of Step S112 (Step S114). Specifically, the reference pupil size determination unit 130 determines the reference pupil size D0 using the reference pupil size table stored in the table storage unit 132. Here, the "reference pupil size" is the size of the pupil diameter, which is changed by a light reflex to the brightness under illumination and the brightness of the object 90. In other words, the reference pupil size is a pupil size in which a change in the pupil size caused by an interest (emotion) of the target person 80 in the object 90 is not considered.

FIG. 7 shows an example of the reference pupil size table according to the first example embodiment. In the reference pupil size table, the incident light amount EE (illuminance) is associated with the reference pupil size. Commonly, the sizes of the pupil diameters at the incident light amounts of 0.01, 1.0, 100, and 10,000 (lx) are 7.0, 6.0, 3.0, and 2.1 (mm), respectively. In this example embodiment, the size of the pupil diameter with respect to the illuminance (the incident light amount) is defined as the reference pupil size. Then, the table storage unit 132 stores the LUT indicating the relationship between the incident light amount (the illuminance) and the reference pupil size as a reference pupil size table.

The reference pupil size determination unit 130 calculates the size of the pupil diameter (the reference pupil size) with respect to the incident light amount EE (the illuminance) using the reference pupil size table shown in FIG. 7. An existing interpolation calculation (interpolation) can be used as the method of calculating the size of the pupil diameter. If a function representing the reference pupil size table can be prepared in advance, the reference pupil size determination unit 130 can calculate the reference pupil size by substituting the incident light amount EE into the function.

The pupil size calculation unit 134 calculates a pupil size D1 of the eye 82 of the target person 80 (Step S116). Specifically, the pupil size calculation unit 134 calculates the pupil size D1 of the eye 82 of the target person 80 who is gazing at the object 90 using the image acquired in the process of S102. More specifically, the pupil size calculation unit 134 detects a pupil area in the eye area specified by the eye area specifying unit 112. The pupil size calculation unit 134 calculates the size of the pupil area. For example, since the diameter of the human iris is as small as about 11 to 12 mm and does not vary much from person to person, the pupil size calculation unit 134 may calculate the pupil size (the pupil diameter) D1 (mm) from a ratio of the pupil diameter (the number of pixels) to the iris diameter (the number of pixels) in the image.

The interest determination unit 140 compares the reference pupil size D0 with the pupil size D1, and determines the interest of the target person 80 in the object 90 (S120 to S124). Specifically, the interest determination unit 140 determines whether or not the pupil size D1 is larger than the reference pupil size D0 (Step S120). If the pupil size D1 is larger than the reference pupil size D0 (YES in Step S120), the interest determination unit 140 determines that the target person 80 is interested in the object 90 (Step S122). On the other hand, if the pupil size D1 is equal to or smaller than the reference pupil size D0 (NO in Step S120), the interest determination unit 140 determines that the target person 80 is not interested in the object 90 (Step S124). The determination result output unit 142 outputs a determination result from the interest determination unit 140 (Step S126).

In the above example, the interest determination unit 140 determines whether or not the target person 80 is interested in the object 90, but the configuration is not limited to this. The interest determination unit 140 may determine a degree of interest of the target person 80 in the object 90. For example, the degree of interest may be expressed by Formula 8 below.

$$(D1 - D0)/D0 \qquad (8)$$

As described above, the interest determination apparatus 100 according to the first example embodiment calculates the amount of light incident on the eyes 82 of the target person 80 using the image captured by the camera 30, and determines the reference pupil size based on the incident light amount. Then, the interest determination apparatus 100 according to the first example embodiment compares the reference pupil size with the pupil size to determine the interest of the target person 80 in the object 90. In this manner, the target person 80 can determine the interest of the target person 80 in the object 90 without wearing special apparatuses such as a luminance meter, an eyeball capturing apparatus, a face capturing apparatus, a visual scene capturing apparatus, and a brightness measuring apparatus. Therefore, the interest determination apparatus 100 according to the example embodiment can determine the interest of the target person in the object under any environment.

The interest determination apparatus 100 according to the first example embodiment is configured to calculate the incident light amount by calculating the luminance of the object 90 using the image of the object 90. In this way, it is possible to determine the interest of the target person 80 in the object 90 without the target person 80 wearing a luminance meter or the like. Even if the object 90 is not a display such as a monitor, the interest of the target person 80 in the object 90 can be determined.

The interest determination apparatus 100 according to the first example embodiment is configured to calculate the incident light amount by calculating the absolute luminance of the object 90 using pixel values in the area of the object 90 in the image. In this way, the incident light amount from the object 90 can be accurately calculated without depending on the setting of the camera 30 or the like.

The interest determination apparatus 100 according to the first example embodiment is configured to calculate the incident light amount by calculating the illuminance in the eyes 82 of the target person 80 using the image. In this way, it is possible to determine the interest of the target person 80 in the object 90 without the target person 80 wearing the brightness measuring apparatus or the like.

The interest determination apparatus 100 according to the first example embodiment is configured to calculate the illuminance in the eyes 82 of the target person 80 using the image, and to calculate the incident light amount based on the luminance of the object 90 and the illuminance in the eyes 82 of the target person 80. Even in environments of the same brightness (illuminance), if the brightness (luminance) of the object 90 to be gazed at are different, the size of the pupil can be different. For example, even in a dark environment where the lighting is dark, if the target person 80 gazes at the bright object 90, the pupil of the target person 80 may become small. Conversely, even in a bright environment where the lighting is bright, if the target person 80 gazes at the dark object 90, the pupil of the target person 80 may become large. Thus, the reference pupil size can be determined more accurately using both the luminance in the object 90 and the illuminance in the eyes 82 of the target person 80. In the first example embodiment, when the reference pupil size is determined, the incident light amount is calculated based on the luminance in the object 90 and the illuminance in the eyes 82 of the target person 80. Therefore, the interest determination apparatus 100 according to the first example embodiment can calculate the incident light amount more accurately, and thus can determine the reference pupil size more accurately. Thus, the interest of the target person 80 in the object 90 can be determined more accurately.

The interest determination apparatus 100 according to the first example embodiment is configured to calculate the illuminance in the eyes 82 of the target person 80 from the color information of the white eye area of the eyes 82 of the target person 80 in the image. In this way, the incident light amount from the environmental light can be accurately calculated using the image.

Modified Example

Note that the present disclosure is not limited to the example embodiment described above, and may be appropriately modified without departing from the purport. For example, the order of the processes in the flowchart shown in FIG. 4 can be changed as appropriate. Further, one or more processes of the flowchart shown in FIG. 4 may be omitted. For example, one or more processes in S104 to S114 may be performed after the process in S116. Further, one or more processes in S104 to S108 may be executed after the process in S110. Furthermore, one of the processes in S108 and S110 may be omitted.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (Read Only Memory), CD-R, CD-R/W, and semiconductor memories (such as Mask ROM, PROM (Programmable ROM), EPROM (Erasable PROM), flash ROM, RAM (Random Access Memory), etc.).

The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Although the present disclosure has been described with reference to the example embodiment, the present disclosure is not limited to the above. The configuration and details of the present disclosure can be modified in various ways that will be understood by those skilled in the art within the scope of the disclosure.

The whole or part of the exemplary embodiments disclosed above can be described as, but not limited to, the following supplementary notes.

(Supplementary note 1)

An interest determination apparatus comprising:
  image acquisition means for acquiring an image obtained by capturing at least eyes of a target person;
  object specifying means for specifying an object in a line-of-sight direction of the target person using the image;
  incident light amount calculation means for calculating an incident light amount representing an amount of light incident on the eyes of the target person using the image;
  reference pupil size determination means for determining a reference pupil size based on the incident light amount;
  pupil size calculation means for calculating a pupil size of the target person using the image; and
  interest determination means for determining an interest of the target person in the object by comparing the reference pupil size with the pupil size.

(Supplementary Note 2)

The interest determination apparatus according to Supplementary note 1, wherein
  the image acquisition means acquires an image obtained by capturing the object, and
  the incident light amount calculation means calculates the incident light amount by calculating luminance in the object using the image.

(Supplementary Note 3)

The interest determination apparatus according to Supplementary note 2, wherein
  the incident light amount calculation means calculates the incident light amount by calculating absolute luminance of the object using a pixel value in an area of the object in the image.

(Supplementary Note 4)

The interest determination apparatus according to Supplementary note 2 or 3, wherein
  the incident light amount calculation means calculates illuminance in the eyes of the target person using the image, and calculates the incident light amount based on the luminance in the object and the illuminance in the eyes of the target person.

(Supplementary Note 5)

The interest determination apparatus according to Supplementary note 1, wherein
  the incident light amount calculation means calculates the incident light amount by calculating illuminance in the eyes of the target person using the image.

(Supplementary Note 6)

The interest determination apparatus according to Supplementary note 4 or 5, wherein
  the incident light amount calculation means calculates the illuminance in the eyes of the target person from color information of a white eye area of the eyes of the target person in the image.

(Supplementary Note 7)

An interest determination system comprising:
at least one imaging apparatus; and
the interest determination apparatus according to any one of Supplementary notes 1 to 6, wherein
the image acquisition means acquires the image captured by the imaging apparatus.

(Supplementary Note 8)

An interest determination method comprising:
acquiring an image obtained by capturing at least eyes of a target person;
specifying an object in a line-of-sight direction of the target person using the image;
calculating an incident light amount representing an amount of light incident on the eyes of the target person using the image;
determining a reference pupil size based on the incident light amount;
calculating a pupil size of the target person using the image; and
determining an interest of the target person in the object by comparing the reference pupil size with the pupil size.

(Supplementary Note 9)

The interest determination method according to Supplementary note 8, further comprising:
acquiring an image obtained by capturing the object; and
calculating the incident light amount by calculating luminance in the object using the image.

(Supplementary Note 10)

The interest determination method according to Supplementary note 9, further comprising:
calculating the incident light amount by calculating absolute luminance of the object using a pixel value in an area of the object in the image.

(Supplementary Note 11)

The interest determination method according to Supplementary note 9 or 10, further comprising:
calculating illuminance in the eyes of the target person using the image, and calculating the incident light amount based on the luminance in the object and the illuminance in the eyes of the target person.

(Supplementary Note 12)

The interest determining method according to Supplementary note 8, further comprising:
calculating the incident light amount by calculating illuminance in the eyes of the target person using the image.

(Supplementary Note 13)

The interest determination method according to Supplementary note 11 or 12, further comprising:
calculating the illuminance in the eyes of the target person from color information of a white eye area of the eyes of the target person in the image.

(Supplementary Note 14)

A non-transitory computer readable medium storing a program causing a computer to execute:
acquiring an image obtained by capturing at least eyes of a target person;
specifying an object in a line-of-sight direction of the target person using the image;
calculating an incident light amount representing an amount of light incident on the eyes of the target person using the image;
determining a reference pupil size based on the incident light amount;
calculating a pupil size of the target person using the image; and
determining an interest of the target person in the object by comparing the reference pupil size with the pupil size.

REFERENCE SIGNS LIST

1 INTEREST DETERMINATION APPARATUS
2 IMAGE ACQUISITION UNIT
4 OBJECT SPECIFYING UNIT
6 INCIDENT LIGHT AMOUNT CALCULATION UNIT
8 REFERENCE PUPIL SIZE DETERMINATION UNIT
10 PUPIL SIZE CALCULATION UNIT
12 INTEREST DETERMINATION UNIT
20 INTEREST DETERMINATION SYSTEM
30 CAMERA
100 INTEREST DETERMINATION APPARATUS
110 IMAGE ACQUISITION UNIT
112 EYE AREA SPECIFYING UNIT
114 LINE-OF-SIGHT DIRECTION ESTIMATION UNIT
116 OBJECT SPECIFYING UNIT
120 INCIDENT LIGHT AMOUNT CALCULATION UNIT
122 OBJECT LUMINANCE CALCULATION UNIT
126 EYE AREA ILLUMINANCE CALCULATION UNIT
130 REFERENCE PUPIL SIZE DETERMINATION UNIT
132 TABLE STORAGE UNIT
134 PUPIL SIZE CALCULATION UNIT
140 INTEREST DETERMINATION UNIT
142 DETERMINATION RESULT OUTPUT UNIT

What is claimed is:

1. An interest determination apparatus comprising:
hardware, including a processor and memory;
an image acquisition unit implemented at least by the hardware and configured to acquire image data obtained by capturing at least eyes of a target person, the image data comprising at least one image;
an object specifying unit implemented at least by the hardware and configured to specify an object in a line-of-sight direction of the target person using the image data;
an incident light amount calculation unit implemented at least by the hardware and configured to calculate an incident light amount representing an amount of light incident on the eyes of the target person using the image data;
a reference pupil size determination unit implemented at least by the hardware and configured to determine a reference pupil size based on the incident light amount;
a pupil size calculation unit implemented at least by the hardware and configured to calculate a pupil size of the target person using the image data; and
an interest determination unit implemented at least by the hardware and configured to determine an interest of the target person in the object by comparing the reference pupil size with the pupil size, wherein
the image data is further obtained by capturing the object, and
the incident light amount calculation unit calculates luminance in the object using the image data, calculates illuminance in the eyes of the target person from color information of a sclera, which is a white eye area of the eyes, of the target person in the image data, and calculates the incident light amount based on the luminance in the object and the illuminance in the eyes of the target person.

2. The interest determination apparatus according to claim 1, wherein
the incident light amount calculation unit calculates the incident light amount further by calculating absolute luminance of the object using a pixel value in an area of the object in the image data.

3. An interest determination method comprising:
acquiring image data obtained by capturing at least eyes of a target person, and by capturing an object, the image data comprising at least one image;
specifying the object in a line-of-sight direction of the target person using the image data;
calculating luminance in the object using the image data;
calculating illuminance in the eyes of the target person from color information of a sclera, which is a white eye area of the eyes, of the target person in the image data; and
calculating an incident light amount representing an amount of light incident on the eyes of the target person using the image data, based on the luminance in the object and the illuminance in the eyes of the target person;
determining a reference pupil size based on the incident light amount;
calculating a pupil size of the target person using the image data; and
determining an interest of the target person in the object by comparing the reference pupil size with the pupil size.

4. The interest determination method according to claim 3, further comprising:
calculating the incident light amount further by calculating absolute luminance of the object using a pixel value in an area of the object in the image data.

5. A non-transitory computer readable medium storing a program causing a computer to execute:
acquiring image data obtained by capturing at least eyes of a target person, and by capturing an object, the image data comprising at least one image;
specifying the object in a line-of-sight direction of the target person using the image data;
calculating luminance in the object using the image data;
calculating illuminance in the eyes of the target person from color information of a sclera, which is a white eye area of the eyes, of the target person in the image data; and
calculating an incident light amount representing an amount of light incident on the eyes of the target person using the image data, based on the luminance in the object and the illuminance in the eyes of the target person;
determining a reference pupil size based on the incident light amount;
calculating a pupil size of the target person using the image data; and
determining an interest of the target person in the object by comparing the reference pupil size with the pupil size.

* * * * *